United States Patent
Bhattacharyya

(10) Patent No.: US 8,754,254 B2
(45) Date of Patent: Jun. 17, 2014

(54) PROCESS FOR PURIFYING TEREPHTHALIC ACID

(75) Inventor: Alakananda Bhattacharyya, Glen Ellyn, IL (US)

(73) Assignee: UOP LLC, Des Plaines, IL (US)

( * ) Notice: Subject to any disclaimer, the term of this patent is extended or adjusted under 35 U.S.C. 154(b) by 549 days.

(21) Appl. No.: 13/155,624

(22) Filed: Jun. 8, 2011

(65) Prior Publication Data

US 2012/0004456 A1    Jan. 5, 2012

Related U.S. Application Data

(60) Provisional application No. 61/360,206, filed on Jun. 30, 2010.

(51) Int. Cl.
*C07C 51/42* (2006.01)

(52) U.S. Cl.
USPC .......................................... 562/485

(58) Field of Classification Search
None
See application file for complete search history.

(56) References Cited

U.S. PATENT DOCUMENTS

| | | |
|---|---|---|
| 2,833,816 A | 5/1958 | Saffer |
| 3,299,125 A | 1/1967 | Ichikawa |
| 3,584,039 A | 6/1971 | Meyer |
| 3,726,915 A | 4/1973 | Pohlman |
| 3,947,494 A | 3/1976 | Kuhlmann |
| 4,323,699 A | 4/1982 | Norval |
| 4,330,676 A | 5/1982 | Moxham |
| 4,380,662 A | 4/1983 | Hanotier |
| 4,394,299 A | 7/1983 | Puskas |
| 4,853,479 A | 8/1989 | Dakka |
| 4,965,406 A | 10/1990 | Dakka |
| 5,081,290 A | 1/1992 | Partenheimer |
| 5,095,146 A | 3/1992 | Zeitlin et al. |
| 5,200,557 A | 4/1993 | Gee et al. |
| 5,354,898 A | 10/1994 | Schroeder |
| 6,137,001 A | 10/2000 | Broeker et al. |
| 6,303,827 B1 | 10/2001 | Saleh et al. |
| 6,320,083 B1 | 11/2001 | Saleh et al. |
| 6,355,835 B1 | 3/2002 | Kulsrestha et al. |
| 6,562,996 B2 | 5/2003 | Saleh |
| 7,094,925 B2 | 8/2006 | Earle et al. |
| 7,196,215 B2 | 3/2007 | Lin |
| 7,449,596 B2 | 11/2008 | Campbell et al. |
| 7,488,843 B1 | 2/2009 | Lee et al. |
| 7,538,237 B2 | 5/2009 | Holl et al. |
| 7,692,036 B2 | 4/2010 | Wonders et al. |
| 2006/0116530 A1 | 6/2006 | Wonders |
| 2007/0010688 A1 | 1/2007 | Ko |
| 2007/0129568 A1 | 6/2007 | Flanagan et al. |
| 2009/0326265 A1 | 12/2009 | Hashmi et al. |
| 2010/0174111 A1 | 7/2010 | Rogers et al. |

FOREIGN PATENT DOCUMENTS

WO    2008151034 A1    12/2008

OTHER PUBLICATIONS

International Search Report and Written Opinion for PCT/US2011/040502 mailed Feb. 21, 2012, Intl. filing date Jun. 15, 2011, Bhattacharyya.
International Preliminary Report on Patentability (IPRP) for PCT/US2011/040502 mailed Jan. 17, 2013, Intl. filing date Jun. 15, 2011, Bhattacharyya.
International Search Report and Written Opinion for PCT/US2011/040515 mailed Feb. 21, 2012, Intl. filing date Jun. 15, 2011, Bhattacharyya.
International Preliminary Report on Patentability (IPRP) for PCT/US2011/040515 mailed Jan. 17, 2013, Intl. filing date Jun. 15, 2011, Bhattacharyya.
International Search Report and Written Opinion for PCT/US2011/040467 mailed Feb. 21, 2012, Intl. filing date Jun. 15,2011, Bhattacharyya.
International Preliminary Report on Patentability (IPRP) for PCT/US2011/040467 mailed Jan. 17, 2013, Intl. filing date Jun. 15, 2011, Bhattacharyya.
International Search Report and Written Opinion for PCT/US2011/040601 mailed Jan. 18, 2012, Intl. filing date Jun. 16, 2011, Bhattacharyya.
International Preliminary Report on Patentability (IPRP) for PCT/US2011/040601 mailed Jan. 17, 2013, Intl. filing date Jun. 16, 2011, Bhattacharyya.
International Search Report and Written Opinion for PCT/US2011/040602 mailed Jan. 18, 2012, Intl. filing date Jun. 16, 2011, Bhattacharyya.
International Preliminary Report on Patentability (IPRP) for PCT/US2011/040602 mailed Jan. 17, 2013, Intl. filing date Jun. 15, 2011, Bhattacharyya.
International Search Report and Written Opinion for PCT/US2011/040474 mailed Feb. 9, 2012, Intl. filing date Jun. 15, 2011, Bhattacharyya.
International Preliminary Report on Patentability (IPRP) for PCT/US2011/040474 mailed Jan. 17, 2013, Intl. filing date Jun. 15, 2011, Bhattacharyya.
International Search Report and Written Opinion for PCT/US2011/040482 mailed Feb. 21, 2012, Intl. filing date Jun. 15, 2011, Bhattacharyya.
International Preliminary Report on Patentability (IPRP) for PCT/US2011/040482 mailed Jan. 17, 2013, Intl. filing date Jun. 15, 2011, Bhattacharyya.
U.S. Appl. No. 13/155,519, filed Jun. 8, 2011, Bhaltacharyya et al.
U.S. Appl. No. 13/155,530, filed Jun. 8, 2011, Bhattacharyya et al.
U.S. Appl. No. 13/155,553, filed Jun. 8, 2011, Bhattacharyya et al.
U.S. Appl. No. 13/155,568, filed Jun. 8, 2011, Bhattacharyya et al.
U.S. Appl. No. 13/155,663, filed Jun. 8, 2011, Bhattacharyya et al.
U.S. Appl. No. 13/155,677, filed Jun. 8, 2011, Bhattacharyya et al.

*Primary Examiner* — Yevegeny Valenrod
(74) *Attorney, Agent, or Firm* — Mark R Willis

(57) ABSTRACT

A process for purifying crude terephthalic acid comprising a contaminant at a first concentration, the process comprising contacting the crude terephthalic acid with a solvent comprising an ionic liquid at purifying conditions to produce a solid terephthalic acid product having a second concentration of the contaminant lower than the first concentration.

19 Claims, No Drawings

PROCESS FOR PURIFYING TEREPHTHALIC ACID

CROSS-REFERENCE TO RELATED APPLICATION

This application claims the benefit of U.S. Provisional Application No. 61/360,206 which was filed on Jun. 30, 2010.

FIELD OF THE INVENTION

This invention relates to processes for purifying crude terephthalic acid by contacting crude terephthalic acid with an ionic liquid to produce a terephthalic acid composition having a lower contaminant content relative to the contaminant content of the crude terephthalic acid.

BACKGROUND OF THE INVENTION

The oxidation of alkyl aromatic compounds, e.g., toluene and xylenes are important commercial processes. A variety of oxidation products may be obtained including aromatic carboxylic acids such as terephthalic acid (1,4-benzenedicarboxylic acid) which is used, for example, in the polymer industry.

U.S. Pat. No. 2,833,816 discloses processes for oxidizing aromatic compounds to the corresponding aromatic carboxylic acids. A process for the liquid phase oxidation of alkyl aromatic compounds uses molecular oxygen, a metal or metal ions, and bromine or bromide ions in the presence of an acid. The metals may include cobalt and/or manganese. Exemplary acids are lower aliphatic mono carboxylic acids containing 1 to 8 carbon atoms, especially acetic acid.

U.S. Pat. No. 6,355,835 discloses a process for the preparation of benzene dicarboxylic acids by liquid phase oxidation of xylene isomers using oxygen or air by oxidising in the presence of acetic acid as solvent, cobalt salt as catalyst and an initiator. The oxidation step is followed by flashing the reaction mixture to remove volatile substances and cooling and filtering to get crude benzene di-carboxylic acid as a solid product and filtrate. Recrystallizing the crude benzene di-carboxylic acid to obtain at least 99% purity and recycling of the filtrate are also disclosed.

U.S. Pat. No. 7,094,925 discloses a process for the oxidation of an alkyl-aromatic compound, wherein the aromatic compound is admixed with an oxidising agent or sulfur compound in the presence of an ionic liquid. Air, dioxygen, peroxide, superoxide, any other form of active oxygen, nitrite, nitrate, nitric acid or other oxides (or oxyhalides) of nitrogen (hydrate or anhydrous) are preferably used as the oxidising agent. The process is usually under Bronsted acidic conditions. The product of the oxidation reaction is preferably a carboxylic acid or ketone or an intermediate compound in the oxidation such as an aldehyde, or alcohol. The oxidation is preferably performed in an ionic liquid containing an acid promoter such as methanesulfonic acid.

US 2009/0326265 A1 discloses a process for preparing an aromatic polycarboxylic acid by liquid phase oxidation of a di- or tri-substituted benzene or naphtalene compound, the process comprising a step of contacting the aromatic compound with an oxidant in the presence of a carboxylic acid solvent, a metal catalyst and a promoter in a reaction zone, wherein the promoter is an ionic liquid comprising an organic cation and a bromide or iodide anion. Advantages of this process include high conversion without severe corrosion problems otherwise associated with halogen-containing compounds as promoter. The process does not necessitate the use of special corrosion-resistant material or liners in the process equipment; thus offering savings on investment and maintenance costs and increasing plant reliability. The process of the invention is especially suited for production of terephthalic acid from p-xylene.

It is also known in the art that the oxidation products such as aromatic aldehydes, aromatic alcohols, aromatic ketones, and aromatic carboxylic acids may solidify or crystallize at oxidation conditions. Thus, mixtures of oxidation products are produced which may require further processing to increase the purity of the desired product. For example, in the production of terephthalic acid, the solid oxidation product is often referred to as crude terephthalic acid as it contains impurities including color bodies, para-toluic acid, and 4-carboxybenzaldehyde (4-CBA) in amounts which make it unacceptable in many polymer applications.

The para-toluic acid and, 4-CBA content of the solid oxidation product may be reduced by washing or dissolving the solid oxidation product in water or other solvents such as acetic acid and methanol and re-solidifying or re-crystallizing the terephthalic acid. However, such processes are typically unable reduce the 4-CBA content sufficiently to meet polymer grade or purified terephthalic acid requirements. To meet purified terephthalic acid quality requirements, conventional purification processes typically reduce the 4-CBA content by reacting a solution of dissolved crude terephthalic acid with hydrogen at hydrogenation conditions usually including a catalyst comprising palladium and carbon. This converts the 4-CBA to para-toluic acid which is then removed by washing and/or dissolution and re-solidifying processes as described above.

U.S. Pat. No. 7,692,036 discloses an optimized process and apparatus for more efficiently and economically carrying out the liquid-phase oxidation of an oxidizable compound. Such liquid-phase oxidation is carried out in a bubble column reactor that provides for a highly efficient reaction at relatively low temperatures. When the oxidized compound is para-xylene and the product from the oxidation reaction is crude terephthalic acid (CTA), such CTA product can be purified and separated by more economical techniques than could be employed if the CTA were formed by a conventional high-temperature oxidation process.

There remains a need in the art for alternate processes that reduce the contaminant levels of crude terephthalic acid. Processes that produce purified terephthalic acid without requiring a hydrogenation and subsequent are desirable as they provide significant capital and operating cost savings.

SUMMARY OF THE INVENTION

In one aspect, the invention provides processes for purifying crude terephthalic acid. Crude terephthalic acid is contacted with an ionic liquid at purifying conditions to produce a terephthalic acid composition having a lower concentration a contaminant relative to the concentration of the contaminant in the crude terephthalic acid In an embodiment, the invention is a process for purifying crude terephthalic acid comprising a contaminant at a first concentration, the process comprising: contacting the crude terephthalic acid with a solvent comprising an ionic liquid at purifying conditions to produce a solid terephthalic acid product having a lower concentration of the contaminant than the first concentration.

In an embodiment, the ionic liquid is selected from the group consisting of an imidazolium ionic liquid, a pyridinium ionic liquid, a phosphonium ionic liquid, a tetra alkyl ammonium ionic liquid, and combinations thereof. In another embodiment, an anion of the ionic liquid anion is selected from the group consisting of halides, acetate, carboxylates, and combinations thereof.

In processes according to the invention, the solvent may further comprise at least one of water and a carboxylic acid having from 1 to 7 carbon atoms. Optionally, terephthalic acid in the crude terephthalic acid is partially or completely dissolved in the solvent.

DETAILED DESCRIPTION OF THE INVENTION

In general, the invention relates to processes for purifying crude terephthalic acid. That is, the invention reduces the level or concentration of at least one contaminant in the crude terephthalic acid. Processes according to the invention may reduce the concentration of multiple contaminants in the crude terephthalic acid. In a broad embodiment, the invention is process for purifying crude terephthalic acid comprising a contaminant at a first concentration, the process comprising contacting the crude terephthalic acid with an ionic liquid at purifying conditions to produce a solid terephthalic acid product having a second concentration of the contaminant lower than the first concentration.

Non limiting examples of contaminants in crude terephthalic acid, include benzoic acid, para-toluic acid, 4-carboxybenzaldehyde (4-CBA), terephthalic aldehyde, para-toluic alcohol, para-tolualdehyde, and 4-carboxybenzylalcohol. As used herein, "crude terephthalic acid" means a terephthalic acid composition having a 4-carboxybenzaldehyde (4-CBA) concentration of more than about 25 ppm-wt and/or a para-toluic acid concentration of more than about 150 ppm-wt, i.e. at least one of the 4-CBA and para-toluic acid concentrations in the crude terephthalic acid is more than 25 ppm-wt and 150 ppm-wt, respectively. As is well known in the art, crude terephthalic compositions may be produced by a wide variety of process including the oxidation of para-xylene to terephthalic acid. It is expected that the instant process will be widely applicable for purifying crude terephthalic acid compositions.

Generally, ionic liquids are non-aqueous, organic salts composed of ions where the positive ion is charge balanced with negative ion. Ionic liquids have low melting points, often below 100° C., undetectable vapor pressure and good chemical and thermal stability. The cationic charge of the salt is localized over hetero atoms, such as nitrogen, phosphorous, sulfur, arsenic, boron, antimony, and aluminum, and the anions may be any inorganic, organic, or organometallic species.

Ionic liquids suitable for use in the instant invention include one or more of imidazolium ionic liquids, pyridinium ionic liquids, tetra alkyl ammonium ionic liquids, and phosphonium ionic liquids. More than one ionic liquid may be used, and multiple ionic liquids may be used in different amounts. Imidazolium, pyridinium, and ammonium ionic liquids have a cation comprising at least one nitrogen atom. Phosphonium ionic liquids have a cation comprising at least one phosphorus atom. In an embodiment the ionic liquid comprises a cation selected from the group consisting of alkyl imidazolium, di-alkyl imidazolium, and combinations thereof. Dialkyl imidazolium ionic liquids have a cation comprising two alkyl groups extending from a five member ring of three carbon and two nitrogen atoms. In an embodiment, the alkyl groups contain from one to eight carbon atoms. There is no need for the two alkyl groups to be the same or have the same number of carbon atoms. The ionic liquid cation may be selected from the group consisting of 1-butyl 3-methyl imidazolium, 1-hexyl 3-methyl imidazolium, and combinations thereof.

In an embodiment, the ionic liquid comprises an anion selected from the group consisting of halides, acetate, carboxylates, and combinations thereof. The ionic liquid may be selected from the group consisting of 1-butyl 3-methyl imidazolium acetate, 1-butyl 3-methyl imidazolium bromide, 1-hexyl 3-methyl imidazolium acetate, 1-hexyl 3-methyl imidazolium bromide, and combinations thereof. In an embodiment, the ionic liquid comprises at least one of 1-butyl-3-methyl imidazolium bromide and 1-butyl-3-methyl imidazolium acetate. In a further embodiment, the ionic liquid comprises at least one of 1-hexyl 3-methyl imidazolium acetate and 1-hexyl 3-methyl imidazolium bromide.

The ionic liquid may be termed a solvent as contact with the crude terephthalic acid at purifying conditions extracts or dissolves or exhibits different solubility for one or more contaminants in the crude terephthalic acid and/or the terephthalic acid. The solvent may comprise additional compounds. In an embodiment, the solvent comprises an ionic liquid selected from the group consisting of an imidazolium ionic liquid, a pyridinium ionic liquid, a phosphonium ionic liquid, a tetra alkyl ammonium ionic liquid, and combinations thereof and at least one of water, an alcohol having from 1 to 7 carbon atoms, and a carboxylic acid having from 1 to 7 carbon atoms. The solvent may comprise an ionic liquid selected from the group consisting of an imidazolium ionic liquid, a pyridinium ionic liquid, a phosphonium ionic liquid, a tetra alkyl ammonium ionic liquid, and combinations thereof, water, an alcohol having from 1 to 7 carbon atoms, and a carboxylic acid having from 1 to 7 carbon atoms. In an embodiment, the solvent comprises an ionic liquid selected from the group consisting of an imidazolium ionic liquid, a pyridinium ionic liquid, a phosphonium ionic liquid, a tetra alkyl ammonium ionic liquid, and combinations thereof and water, and optionally, an alcohol having from 1 to 7 carbon atoms or a carboxylic acid having from 1 to 7 carbon atoms. In another embodiment, the solvent comprises an ionic liquid selected from the group consisting of an imidazolium ionic liquid, a pyridinium ionic liquid, a phosphonium ionic liquid, a tetra alkyl ammonium ionic liquid, and combinations thereof and a carboxylic acid having from 1 to 7 carbon atoms, and optionally, an alcohol having from 1 to 7 carbon atoms. The solvent may comprise an ionic liquid selected from the group consisting of an imidazolium ionic liquid, a pyridinium ionic liquid, a phosphonium ionic liquid, a tetra alkyl ammonium ionic liquid, and combinations thereof and an alcohol having from 1 to 7 carbon atoms. In an embodiment, the carboxylic acid of the solvent is acetic acid. In another embodiment the alcohol of the solvent is methanol.

In an embodiment, the solvent comprises an ionic liquid selected from the group consisting of an imidazolium ionic liquid, a pyridinium ionic liquid, a phosphonium ionic liquid, a tetra alkyl ammonium ionic liquid, and combinations thereof and at least one of water, methanol, and acetic acid. The solvent may comprise an ionic liquid selected from the group consisting of an imidazolium ionic liquid, a pyridinium ionic liquid, a phosphonium ionic liquid, a tetra alkyl ammonium ionic liquid, and combinations thereof, water, methanol, and acetic acid. In an embodiment, the solvent comprises an ionic liquid selected from the group consisting of an imidazolium ionic liquid, a pyridinium ionic liquid, a phosphonium ionic liquid, a tetra alkyl ammonium ionic liquid, and combinations thereof and water, and optionally, methanol or acetic acid. In another embodiment, the solvent comprises an ionic liquid selected from the group consisting of an imidazolium ionic liquid, a pyridinium ionic liquid, a phosphonium ionic liquid, a tetra alkyl ammonium ionic liquid, and combinations thereof and acetic acid, and optionally, methanol. The solvent may comprise an ionic liquid selected from the group consisting of an imidazolium ionic liquid, a pyridinium ionic liquid, a phosphonium ionic liquid, a tetra alkyl ammonium ionic liquid, and combinations thereof and methanol.

In an embodiment, the crude terephthalic acid is contacted with the entire solvent. Contacting of the solvent and crude terephthalic acid may occur in stages or steps. The solvent may be divided into or formed in two or more portions having the same or different compositions and the contacting may be performed stepwise. For example, crude terephthalic acid may be contacted with, or partially dissolved in, or dissolved in a first portion of the solvent and the resulting mixture is then contacted with a second portion of the solvent. The ionic liquid may be in the first or the second or both portions of the solvent. The solvent may contain more than one carboxylic acid and/or more than one alcohol.

In an embodiment, the solvent has a ratio of ionic liquid to carboxylic acid ranging from about 1:1000 to about 1000:1 by weight. In another embodiment, the solvent further comprises water and the solvent has a ratio of ionic liquid to water ranging from about 1:1000 to about 1000:1 by weight. In an embodiment, the ratio of solvent to crude terephthalic acid ranges from about 10:1 to about 1:1 by weight.

The invention may be practiced in laboratory scale experiments through full scale commercial operations. The process may be operated in batch, continuous, or semi-continuous mode. The invention requires that the crude terephthalic acid be contacted with an ionic liquid at purifying conditions. However, as described above, the solvent may be formed in several steps and crude terephthalic acid may be contacted with portions of the solvent in different steps or stages. When the solvent comprises more than one component, the order of addition of the components and/or the order of contacting the solvent components with the crude terephthalic acid is not essential to the invention.

The solvent provides a liquid phase for the extraction or dissolution or partial dissolution of one or more contaminants from the crude terephthalic acid. The solvent may also dissolve or partially dissolve the terephthalic acid present. The solvent may be formed prior to the contacting step, in the same or different vessel as that used in the contacting step. In another embodiment, the solvent is formed in the contacting vessel, e.g. adding various streams of the solvent components individually and/or in combination to a continuous or semi-continuous contacting vessel. The crude terephthalic acid may be added to the contacting vessel as a solid. In an embodiment, the crude terephthalic acid is added to the contacting vessel as a slurry with or dissolved in or partially dissolved in one or more of the solvent streams being added to the vessel. The solvent or various streams of the solvent components may be heated before they are mixed together or contacted with the crude terephthalic acid.

Conventional, liquid phase solvent contacting vessels as known in the art such as crystallizers may be used to practice the invention. Other examples include vessels, which may have one or more mechanical agitators, and various solvent contacting, liquid-liquid and liquid solid extraction vessels. Agitation or mixing may be provided by turbulent fluid flow. It is also well known in the art to design, operate, and control such contacting vessels in the production of crude and purified terephthalic for the purification conditions employed including, e.g., the temperature, pressure, and the potential corrosive nature of some contaminants such as bromine that may be present in the crude terephthalic acid. See, e.g. U.S. Pat. No. 7,692,036 and U.S. Pat. No. 6,137,001.

Purification conditions of the invention generally include a temperature ranging from about 20° C. to about 275° C. and a pressure ranging from about atmospheric to about 4.0 MPa (g) and a residence time ranging from about 5 seconds to about 10 hours. In another embodiment, the temperature ranges from about 50° C. to about 225° C. In a further embodiment, the residence time ranges from about 2 minutes to about 2 hours. The purification temperature, pressure and residence time may vary based on a variety of factors including for example, the reactor configuration, size, and whether the process is, batch, continuous, or semi-continuous. A purification condition may also vary based on other purification condition. For example, use of a particular temperature range may enable use of a different residence time range.

The invention produces a solid terephthalic acid product, which may precipitate, crystallize, or solidify in the liquid phase solvent mixture at the purifying conditions and/or as the mixture cools. The operating conditions may be changed within the range of purification conditions to facilitate solidification of the terephthalic acid product. In another embodiment, the contaminant may be extracted from the solid crude terephthalic acid leaving the remaining extracted solid as the solid terephthalic acid product.

Without wishing to be bound by any particular theory, it is believed that the use of ionic liquids according to the invention alters the solubility of terephthalic acid and/or at least one of the partially oxidized para-xylene intermediates present in the crude terephthalic acid. In an embodiment, the invention reduces at least the concentration of 4-carboxybenzaldehyde in the solid terephthalic acid product. In another embodiment, the invention reduces the concentration of one or more other partially oxidized para-xylene compounds in the crude terephthalic acid. The invention may reduce the concentration of 4-carboxybenzaldehyde and para-toluic acid in the crude terephthalic acid. The invention may reduce the concentration of all the partially oxidized para-xylene compounds in the crude terephthalic acid.

The invention does not require, but encompasses the use of multiple solvent contacting steps. The terephthalic acid product from an individual solvent contacting step may, but is not required to be, solidified before introduction into a subsequent solvent contacting step. In an embodiment, a second solvent contacting step includes a second purifying temperature that is lower than the purifying temperature of the first solvent contacting step. When used, an additional solvent contacting step may be according to the invention or the invention may be combined with conventional solvent contacting and/or re-crystallization steps known in the art.

In an embodiment, the invention further comprises separating the solid terephthalic acid product from the solvent to produce a spent solvent and a separated solid terephthalic acid product. The separating step may be accomplished for example by filtration and/or centrifugation and/or settling. The spent solvent may be recycled and reused in the contacting step and/or oxidation step of a crude terephthalic acid production process.

The separated solid terephthalic acid product may be washed with water and/or a carboxylic acid having from 1 to 7 carbon atoms to produce a washed solid terephthalic acid product. Washing conditions may include a temperature ranging from about 20° C. to about 275° C. and a pressure ranging from about atmospheric to about 4.0 MPa(g). In an embodiment, the washed terephthalic acid product is dried as known in the art to provide a dried terephthalic acid product. Optionally, the separated solid terephthalic acid product or the washed solid terephthalic acid product or the dried terephthalic acid product may be hydrogenated. Such separating, washing, drying, hydrogenation, and subsequent processing steps have been described in the general literature and are well known to those of ordinary skill in the art of purifying terephthalic acid compositions.

In another embodiment, the invention excludes all hydrogenation steps. Thus, the invention enables a simpler and less costly purification process relative to conventional processes. In an embodiment, the invention further comprises processing steps subsequent to the solvent contacting step, which are selected from the group of process steps consisting of washing, separating, drying, solvent contacting, and combinations thereof. The invention enables the production of a dried terephthalic acid product having a concentration of 4-carboxybenzaldehyde of no more than 25 ppm-wt. In another embodiment, the dried terephthalic acid product has a concentration of para-toluic acid of no more than 150 ppm-wt. In a further embodiment, the dried terephthalic acid product meets polymer grade or purified terephthalic acid purity requirements.

The invention claimed is:

1. A process for purifying crude terephthalic acid comprising a contaminant at a first concentration, the process comprising: contacting the crude terephthalic acid with a solvent at purifying conditions to produce a solid terephthalic acid product having a second concentration of the contaminant lower than the first concentration wherein the solvent comprises an ionic liquid and a carboxylic acid having from 1 to 7 carbon atoms and the solvent has a ratio of ionic liquid to the carboxylic acid ranging from about 1:1000 to about 1000:1 by weight.

2. The process of claim 1 wherein the ionic liquid is selected from the group consisting of an imidazolium ionic liquid, a pyridinium ionic liquid, a phosphonium ionic liquid, a tetra alkyl ammonium ionic liquid, and combinations thereof.

3. The process of claim 1 wherein the ionic liquid is an imidazolium ionic liquid, and the solvent comprises a second ionic liquid selected from the group consisting of a second imidazolium ionic liquid, a pyridinium ionic liquid, a phosphonium ionic liquid, and a tetra alkyl ammonium ionic liquid.

4. The process of claim 1 wherein an anion of the ionic liquid is an anion selected from the group consisting of halides, acetate, carboxylates, and combinations thereof.

5. The process of claim 1 wherein the ionic liquid cation is selected from the group consisting of 1-butyl 3-methyl imidazolium, 1-hexyl 3-methyl imidazolium, and combinations thereof.

6. The process of claim 1 wherein the ionic liquid is selected from the group consisting of 1-butyl 3-methyl imidazolium acetate, 1-butyl 3-methyl imidazolium bromide, 1-hexyl 3-methyl imidazolium acetate, 1-hexyl 3-methyl imidazolium bromide, and combinations thereof.

7. The process of claim 1 wherein the solvent further comprises at least one of water, and an alcohol having from 1 to 7 carbon atoms.

8. A process for purifying crude terephthalic acid comprising a contaminant at a first concentration, the process comprising: contacting the crude terephthalic acid with a solvent comprising an ionic liquid at purifying conditions to produce a solid terephthalic acid product having a second concentration of the contaminant lower than the first concentration wherein the solvent further comprises acetic acid.

9. The process of claim 1 wherein the solvent further comprises water and the solvent has a ratio of ionic liquid to water ranging from about 1:1000 to about 1000:1 by weight.

10. The process of claim 1 wherein the purifying conditions comprise a pressure ranging from about atmospheric to about 4.0 MPa(g).

11. The process of claim 1 wherein the purifying conditions comprise a temperature ranging from about 20° C. to about 275° C.

12. The process of claim 1 wherein a ratio of the solvent to the crude terephthalic acid ranges from about 1:1 to about 10:1 by weight.

13. The process of claim 1 wherein the purifying conditions comprise mixing the crude terephthalic acid and the solvent.

14. The process of claim 1 wherein the contaminant is one or both of para-toluic acid and 4-carboxybenzaldehyde.

15. The process of claim 1 wherein terephthalic acid in the crude terephthalic acid is partially or completely dissolved in the solvent.

16. The process of claim 15 wherein the process further comprises forming the terephthalic acid product as a solid in the solvent.

17. The process of claim 16 wherein the terephthalic acid product is formed as a solid at a second temperature, the second temperature being lower than a purification temperature.

18. The process of claim 16 further comprising separating the solid terephthalic acid product from the solvent to produce a separated solid terephthalic acid product.

19. The process of claim 18 further comprising drying, and optionally washing, the separated solid terephthalic acid product to produce a dried terephthalic acid product.

* * * * *